(12) United States Patent
Choudhary et al.

(10) Patent No.: US 10,568,336 B2
(45) Date of Patent: Feb. 25, 2020

(54) COMPLETE YOGURT MAKER APPLIANCE

(71) Applicant: Jogurt, LLC, Milpitas, CA (US)

(72) Inventors: Prashant Choudhary, Milpitas, CA (US); Suresh Chandrasekaran, Bangalore (IN)

(73) Assignee: JOGURT, LLC, Milpitas, CA (US)

( * ) Notice: Subject to any disclaimer, the term of this patent is extended or adjusted under 35 U.S.C. 154(b) by 24 days.

(21) Appl. No.: 15/368,029

(22) Filed: Dec. 2, 2016

(65) Prior Publication Data

US 2017/0156358 A1    Jun. 8, 2017

Related U.S. Application Data

(60) Provisional application No. 62/262,370, filed on Dec. 2, 2015.

(51) Int. Cl.
| | |
|---|---|
| *A23C 9/12* | (2006.01) |
| *C12M 1/36* | (2006.01) |
| *C12M 1/02* | (2006.01) |
| *C12M 1/06* | (2006.01) |
| *A47J 43/046* | (2006.01) |

(52) U.S. Cl.
CPC .......... *A23C 9/1223* (2013.01); *A47J 43/046* (2013.01); *C12M 27/06* (2013.01); *C12M 41/18* (2013.01); *C12M 41/22* (2013.01); *C12M 41/48* (2013.01)

(58) Field of Classification Search
CPC ..... A23C 9/1223; A47J 43/046; C12M 41/18; C12M 41/22; C12M 27/06; C12M 41/48
USPC .................. 99/452, 453, 331–332, 325–327, 99/352–353, 357, 468, 470; 366/144–147
See application file for complete search history.

(56) References Cited

U.S. PATENT DOCUMENTS

| | | | |
|---|---|---|---|
| 3,685,153 A | 8/1972 | Borkton | |
| 5,363,746 A | 11/1994 | Gordon | |
| 6,213,007 B1 | 4/2001 | Lande | |
| 2008/0066628 A1 | 3/2008 | Yushen et al. | |
| 2008/0307240 A1 | 12/2008 | Dalian et al. | |
| 2009/0260527 A1 | 10/2009 | Qian et al. | |
| 2009/0280214 A1 | 11/2009 | Boo et al. | |
| 2013/0269540 A1 | 10/2013 | Lazzarini et al. | |

FOREIGN PATENT DOCUMENTS

| | | |
|---|---|---|
| DE | 1757273 | 4/1971 |
| GB | 1582113 | 12/1981 |
| WO | 2015/063094 A1 | 5/2015 |

*Primary Examiner* — Michael G Hoang
(74) *Attorney, Agent, or Firm* — Law Office of Dorian Cartwright; Dorian Cartwright (57) ABSTRACT

A yogurt maker device comprises an outer shell to house a yogurt vessel that receives milk and a culture container that receives yogurt culture. A processor within the outer shell controls a heating element to boil milk within the yogurt vessel using a temperature sensor as feedback and for maintaining a predefined boiling temperature for a predefined period of boiling time and a stirring device to continuously stir boiling milk within the yogurt vessel while boiling and also while cooling to a cooling predefined temperature until fermentation temperature is reached. The processor also controls a culture container base holding the culture container and having a motor to automatically pour the yogurt culture when the fermentation temperature is reached. Finally, a cooling mechanism automatically provides cooling to contents of the yogurt vessel once fermentation is complete.

13 Claims, 8 Drawing Sheets

COMPLETE YOGURT MAKER APPLIANCE

CROSS-REFERENCE TO RELATED APPLICATIONS

This application claims priority under 35 USC 119(e) to U.S. Application No. 62/262,370, filed on Dec. 2, 2015 by Prashant Choudhary, et al. and entitled FULLY AUTONOMOUS YOGURT MAKER APPLIANCE, the content of which is being incorporated herein by reference in their entirety.

FIELD OF THE DISCLOSURE

The invention relates generally to autonomous cooking devices, and more specifically, to a single appliance to completely prepare yogurt with a single process from a user perspective.

BACKGROUND OF DISCLOSURE

Yogurt making at home is a tedious process comprising of multiple preparation steps starting from slowly boiling milk to approximately 180 Fahrenheit while stirring continuously for 20 minutes or more to break down milk proteins and prevent clumping. Subsequently, milk is allowed to cool down to fermentation temperature of around 110 F, at which point culture is stirred into the milk. The milk and culture mixture is then stored in an insulated constant temperature environment for a fixed amount of time which can vary from 6 to 12 hours or more. After yogurt is thus fermented for the stipulated time, it needs to be transferred to refrigerator otherwise it may turn sour. Furthermore, to make a thicker yogurt another manual step of straining to separate liquid whey may be required. Thus, all these steps require careful human attention to achieve good results.

Existing yogurt makers in the market mostly help in the last phase of the yogurt making process by providing a constant temperature environment for optimal fermentation. However, there is no single device which can handle all the steps of yogurt making.

Current techniques of home yogurt making require several different devices. One cooking device (e.g., a pot or other cooking appliance) is needed to boil milk. A separate culture device is needed for yogurt culture to be kept at an appropriate temperature until combined with the milk. Otherwise, in an appliance which will also boil the milk, the temperature will reach high levels and the yogurt culture can potentially be destroyed and consequentially prevent fermentation. A mixer device is needed to combine the yogurt culture and milk. If skin forms on the milk surface, it can cause boil-over and also give a bad texture to the yogurt. Yet another refrigeration device is needed to refrigerate fermented yogurt. Each device functionality places a significant load on the power supply (e.g., a cooking device, a heating device, a mixer device, and a refrigeration device. Further, a device which handles milk can be hard to wash and may develop smell issues over time for any parts exposed to milk.

It is highly desirable to overcome shortcomings of the existing multitude of yogurt maker devices and to overcome all the challenges of integrating multiple steps of yogurt making. It is further desirable for a robust autonomous cooking device to automatically prepare yogurt in a single process from a user perspective.

SUMMARY

These shortcomings are addressed by the present disclosure of devices, and related computer readable media and methods for an autonomous cooking device to automatically prepare yogurt in a single process.

In an embodiment, a yogurt maker device comprises an outer shell to house a yogurt vessel that receives milk and a culture container that receives yogurt culture. An input/output device accessible from the outer shell, the input/output device to receive a selection of yogurt recipe parameters.

Another embodiment includes a processor within the outer shell. A heating element, controlled by the processor, boils milk within the yogurt vessel using a temperature sensor as feedback and for maintaining a predefined boiling temperature for a predefined period of boiling time. A stirring device, controlled by the processor, continuously stirs boiling milk within the yogurt vessel while boiling and also while cooling down to fermentation temperature, and further, while mixing the yogurt culture into the milk.

In other embodiments, a culture container base holding the culture container and having a motor communicatively coupled to the processor, automatically pours the yogurt culture when the fermentation temperature is reached. Finally, a cooling mechanism, controlled by the processor, automatically provides cooling (e.g., with a Peltier block) to contents of the yogurt vessel once fermentation is complete.

Advantageously, a single device of small form factor removes the user complexity of making yogurt with a single autonomous process from the user perspective.

DESCRIPTION OF FIGURES

In the following drawings, like reference numbers are used to refer to like elements. Although the following figures depict various examples of the invention, the invention is not limited to the examples depicted in the figures.

DETAILED DESCRIPTION OF THE DISCLOSURE

Autonomous yogurt maker devices, and related computer-readable media, and methods, are described. At a high-level, the autonomous device is prepped only with raw ingredients for yogurt. Those ingredients are automatically boiled, fermented, and refrigerated, all in the same device during a single process from a user perspective. Subsequently, fully prepared, refrigerated yogurt is processed from the ingredients by the device. A compact form factor helps for easy storage and deployment.

Many other aspects of the device are possible within the spirit of the present invention, as will be apparent to one of ordinary skill in the art. Also, the techniques can be modified by one of ordinary skill in the art, within the spirit of the current invention, for example, to apply the techniques to different types of yogurt (e.g., Greek) or different dishes (e.g., making ice cream). Accordingly, the following details are non-limiting and are set forth only for the purpose of illustration of preferred embodiments which can be varied within the spirit of the current invention by those of ordinary skill in the art.

I. Various Embodiments of Yogurt Maker Devices

Figure 1:
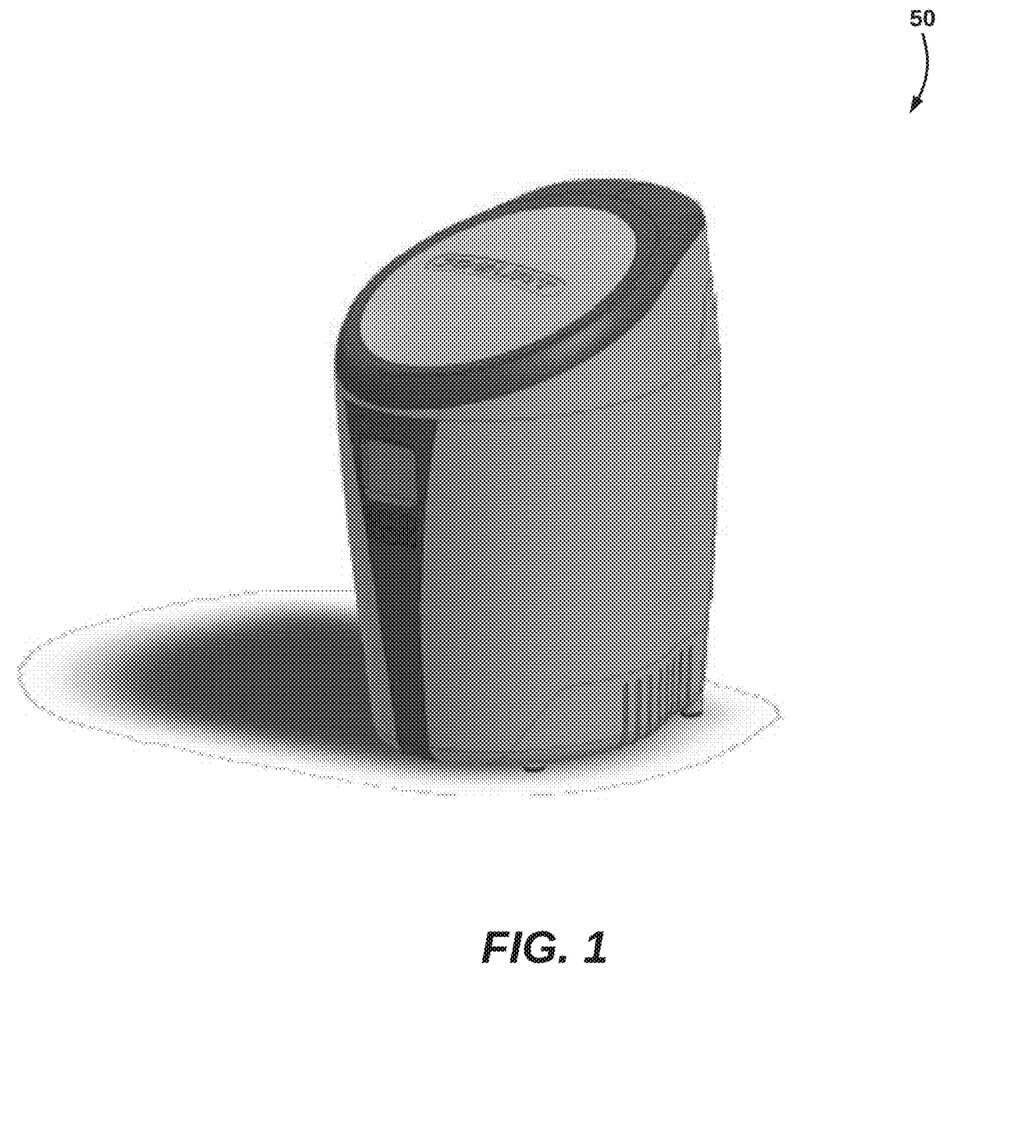
FIG. 1 is a schematic diagram of an exterior shell of a yogurt maker device, according to an embodiment.

FIG. 1 is a schematic diagram of an exterior shell of a yogurt maker device 50, according to an embodiment. Specifically, FIG. 1 shows one design of the yogurt maker 50 that mixes organic forms with a modern aesthetic. Fully automated, a lid assembly slides open revealing an interior yogurt vessel, mixer, and culture container, as described more fully below with respect to subsequent figures. A user interface includes a digital screen (e.g., a touch screen) along with buttons used for adjusting settings as executed by internal electronics and software. A gradient texture at the bottom and optionally in the rear hides vents while providing a visually appealing look. The yogurt maker 50 is upright and supported by four legs, but can also have different orientations. A small form factor, for example, comparable to a blender or a crock pot, limits the amount of counter space during use and the amount of storage space during when not in use.

Figure 2:
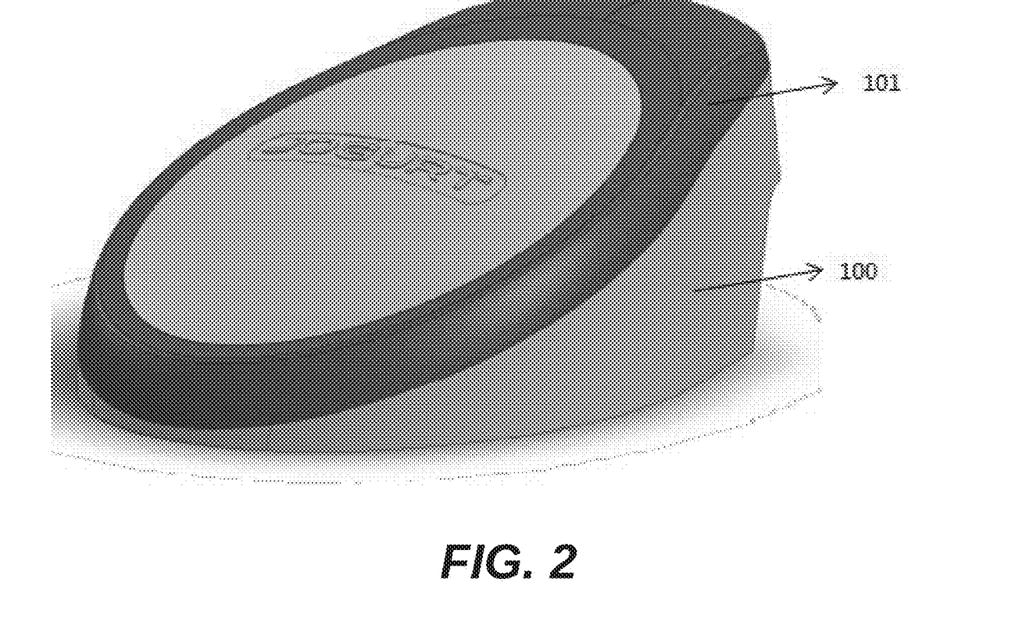
FIG. 2. is a schematic diagram illustrating a detachable lid base for the yogurt maker device, according to an embodiment.

FIG. 2. is a schematic diagram illustrating a detachable lid base 100 for the yogurt maker device 50, according to an embodiment. The lid base 100 can be easily attached or detached from the yogurt maker device 50 for easy cleaning of the lid base 100 and internals.

Figure 3:
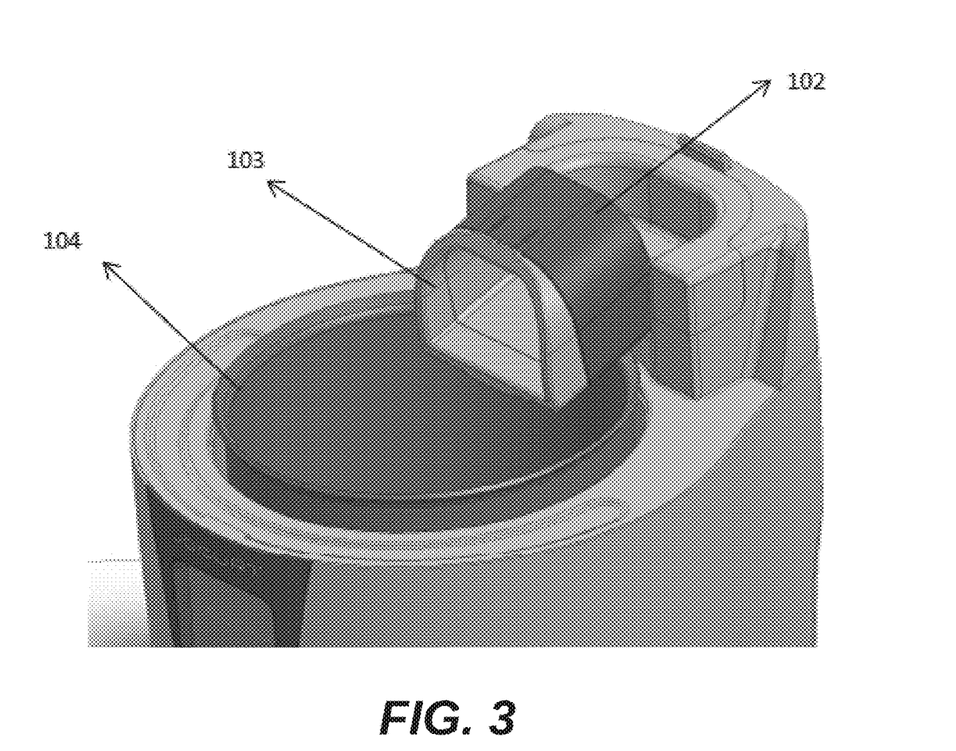
FIG. 3 is a schematic diagram illustrating a dispenser and a bowl of the yogurt maker device, according to an embodiment.
Figure 4A:
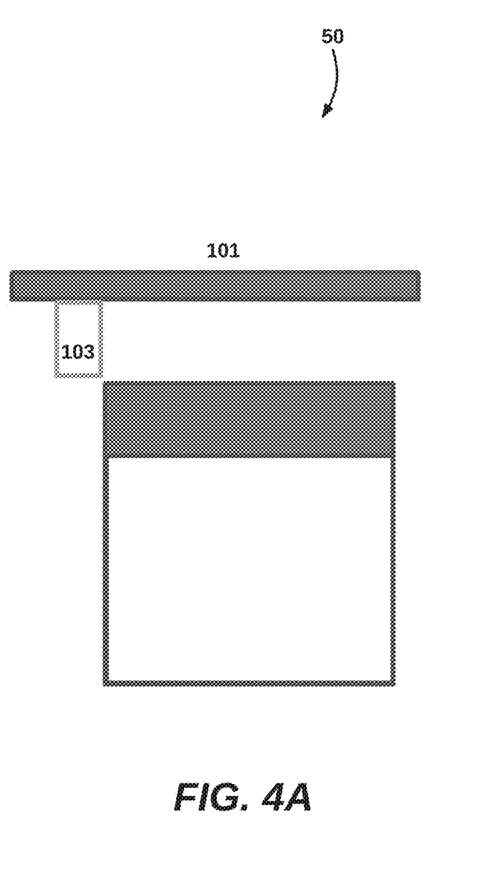
FIGS. 4A-4B are block diagrams illustrating the detachable lid base in open and closed positions, according to an embodiment.
Figure 4B:
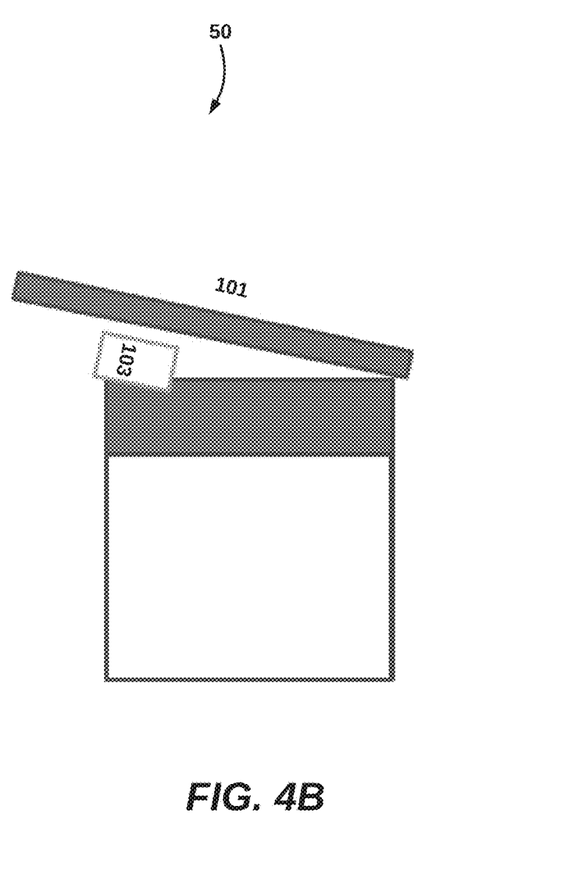

A top lid flap 101 covers contents of the inner container, as shown in FIG. 3. More specifically, a yogurt vessel 104 is positioned below a culture container base 102. One example of the top lid flap 101, as shown in FIGS. 4A-B, specifically covers a culture container 103 within the culture container base 102 for protection against hot vapors of boiling milk. Vapors from boiling milk can also escape from the opening and/or vents, and the top lid flap 101 insulates the contents from hot vapors rising out of boiling milk. When the culture container base 102 tilts to pour contents of the culture container 103 into the yogurt vessel 104, the top lid flap 101 closes to seal the fermentation process.

In one embodiment, vents in the top lid flap 101 also allows steam from boiling milk to escape and for faster cooling. In another embodiment, the top lid flap 101 holds a stirrer along with mechanics and electronics for stirrer operation. The top lid flap 101 is naturally held in horizontal position when the culture dispenser 103 is in vertical position. In the horizontal position the lid flap 101 seals the culture from surrounding heat as well as lets the heat vent out. When the culture container 103 is automatically tilted from the vertical position by a motor into the yogurt vessel 104 for dispensing the culture (see FIG. 4A versus FIG. 4B) (to the same tilted position of FIG. 3), the top lid flap 101 automatically closes providing the anaerobic environment for successful fermentation process (to the same closed position of FIG. 2). The venting of vapors for extended period allows for a thicker consistency of yogurt. Thus, the user can make Greek yogurt without going through an additional step of straining the yogurt to separate out the whey. In another embodiment, no venting or limited venting is allowed which results in a more watery yogurt.

The yogurt vessel 104 can be formed from a ferrous material such as stainless steel, non-ferrous materials, polymers, or any other material that can withstand the temperature and stirring conditions. The purpose of the yogurt vessel 104 is to hold the ingredients being combined, such as milk, yogurt culture, water, and flavors. The yogurt vessel 104 is preferably suited to handle a range of temperatures from boiling to refrigeration. The yogurt vessel 104 can be removable for washing or replacement as needed. A stirring mechanism is integrated at the bottom of vessel 104 to allow better mixing of ingredients.

Many variations are possible. For example, a curved base 203 of the yogurt vessel 104 can provide room for a stirring mechanism to be placed on a flat base so that the yogurt making device 50 can be placed on a flat surface without toppling. One embodiment rotates the yogurt vessel 104 itself to help in stirring and no mixing mechanism is integrated in the vessel. Some implementations have additional containers besides the culture container 103 (e.g., artificial flavoring or seasoning containers).

An aluminum vessel enclosure 200 forms the outer shell, in this embodiment, and can alternatively be made from any other metallic material with good thermal conductivity. The body can be self-supporting or can be attached to a metallic supporting frame. An insulating layer is disposed between an inner container 201 and the outer shell to separate a cooking environment from the outside and the contents of vessel are thermally insulated from the outside environment. A central processing unit, computer memory, and a computer display can be integrated within the outer shell, also isolated from the cooking environment in order to protect the electronics. The display can be a touch screen or have push buttons to receive input directly from a user, and to display conditions from within.

Figure 5:
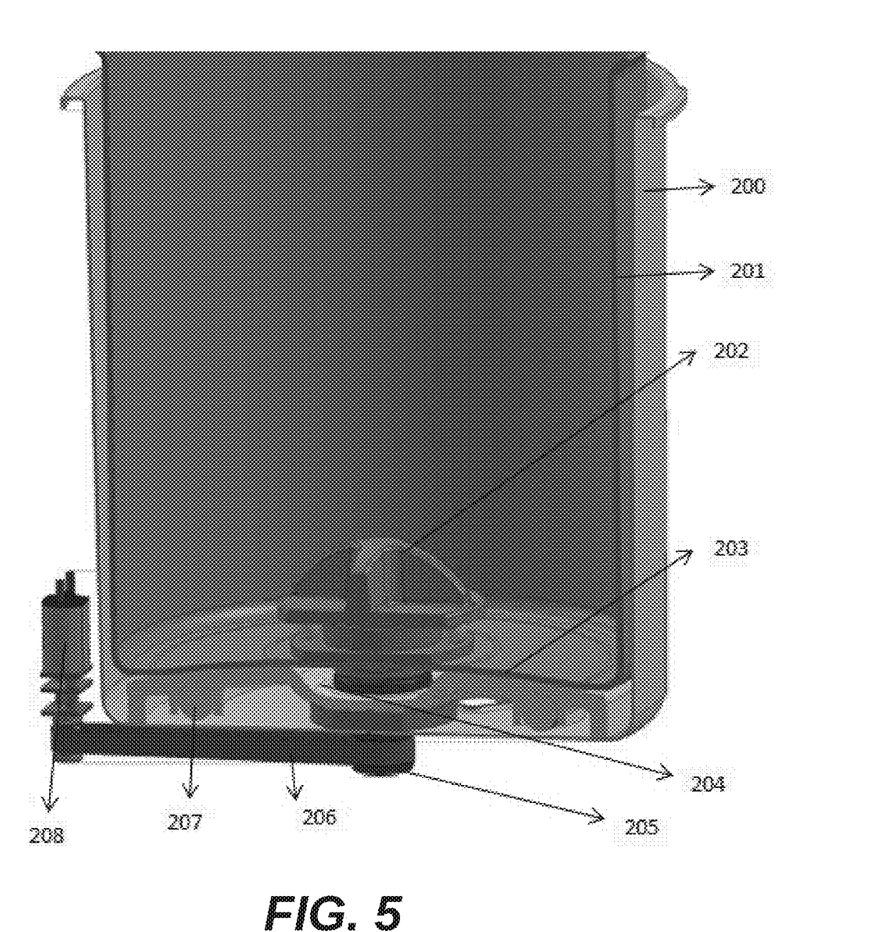
FIG. 5 is a schematic diagram illustrating a stirring blade of the yogurt maker device, according to an embodiment.

FIG. 5 is a schematic diagram illustrating a stirring blade 202 of the yogurt maker device 50, according to an embodiment.

The stirring blade 202 circulates ingredients in the yogurt vessel 104 and also keeps temperature uniform. The stirring blade 202 creates a vortex on milk surface and prevents skin formation during boiling. Different shapes, such as ovals and diamonds can be utilized to optimize stirring. A standard Kitchen-Aid style mixing blade can also be used. For example, a slanted stirrer helps move ingredients from top to bottom. In some embodiments, the stirring blade 202 is removable for cleaning and changing. A stepper motor or DC servo motor drives the stirrer blade 202 via a stirrer shaft 205 using electric power. More specifically, a polyurethane drive belt 206 couples a motor 208 to the stirrer shaft 205, without transferring significant heat back to the motor. This prevents motor overheating.

Figure 6:
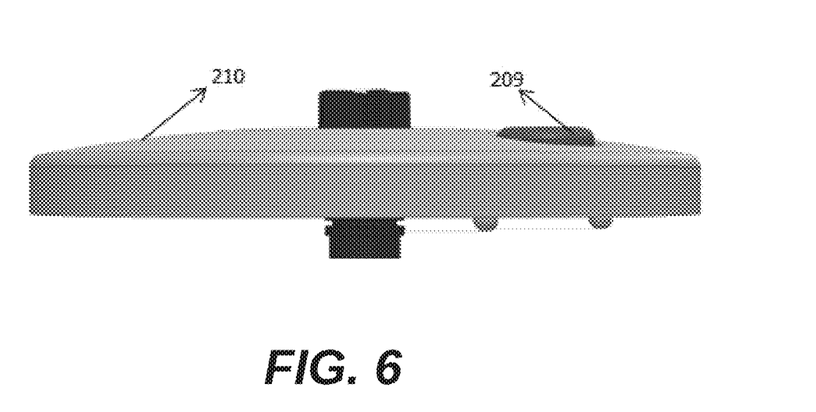
FIG. 6 is a schematic diagram illustrating a heating plate of the yogurt maker device, according to an embodiment.

Milk is heated by a heating coil 207 coupled to a heating element 210 or heating plate to distribute heat, as shown in FIG. 6. The heating coil 207 can be a resistance heater, an induction heater, a heating plate, a heating coil, or the like. An air pocket 204 provides thermal insulation from heat and prevents the stirrer shaft 205 from overheating. In some embodiments, a temperature sensor 209 or thermocouple is positioned on the heating plate 210 or near the stirring blade 202 for feedback on ingredient temperature. As a result, the yogurt maker device 50 can determine when certain temperature ranges have been reached for boiling, fermentation, and refrigeration. In one embodiment the heating element can be placed on the sides of the vessel. In yet another embodiment inductive or solid state heating can be used instead of heating element.

Figure 7:
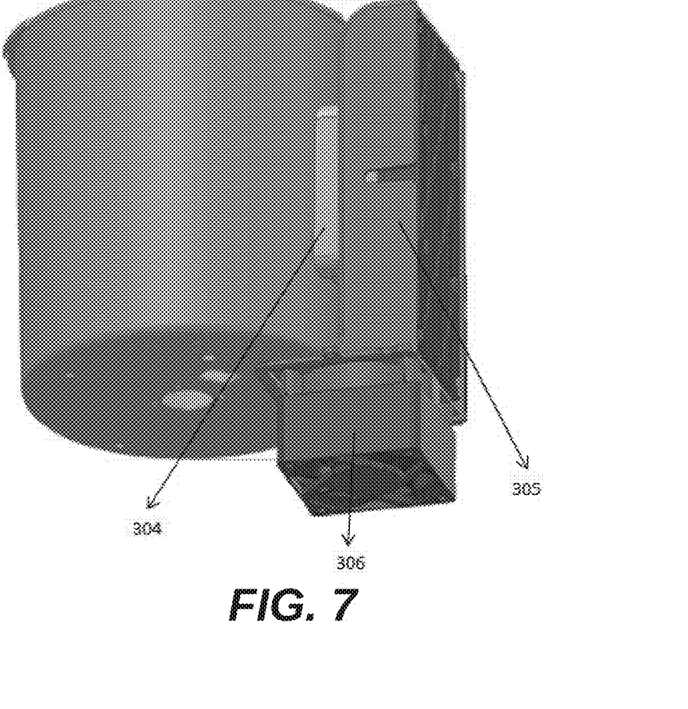
FIGS. 7-8 are schematic diagrams illustrating a cooling mechanism of the yogurt maker device, according to an embodiment.
Figure 8:
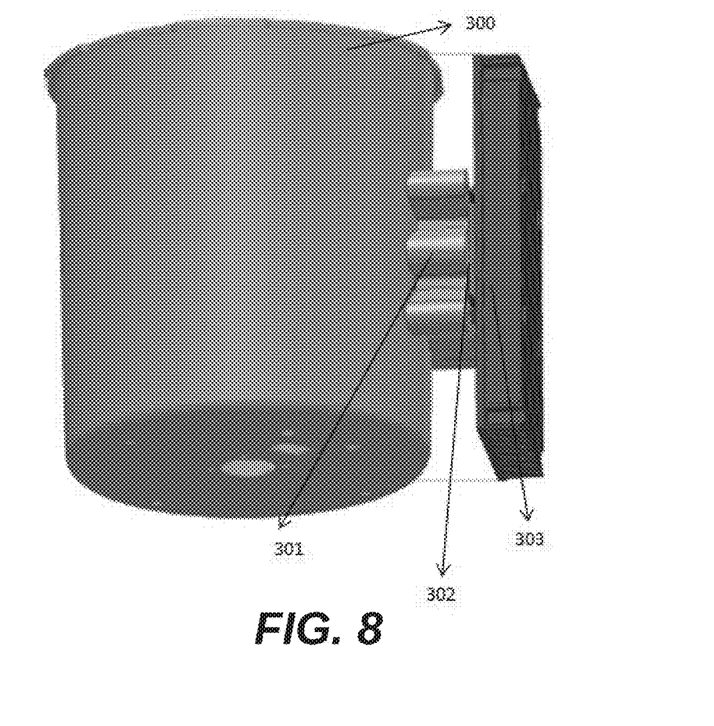

FIGS. 7-8 are schematic diagrams illustrating a cooling mechanism of the yogurt maker device, according to an embodiment.

The cooling mechanism can include exhaust fans 306 attached to a vessel enclosure 300 to create airflow through air duct 305, and thus removing waste heat from heat-sink. The inner heat sink 301 is curved from one side to efficiently transfer heat from the inner vessel to cold side of Peltier module 302. The Peltier module transfers heat from cold side to the hot side which is in thermal contact with bigger heat-sink 303. Cool air is pulled from the bottom and thrown onto the outer heat-sink. As cool air flows over the heat-sink, it warms up as it collects waste heat and finally exits out from a top vent. In another embodiment, the fan is placed on top of the outer heat-sink and it sucks hot air from the outer heat-sink and throws it out while cool air from the bottom replaces the sucked out hot air.

For further cooling down to 40 degrees Fahrenheit for refrigeration, or for faster cooling than the fans, cooling pads or Peltier chips 302 can be used. The Peltier chips are thermoelectric coolers that create a heat flux between the junction of two different types of materials. Peltier chips are solid state and thus have no moving parts which allow smaller form factors. Other types of cooling (e.g., refrigeration) can also be implemented.

Figure 9:
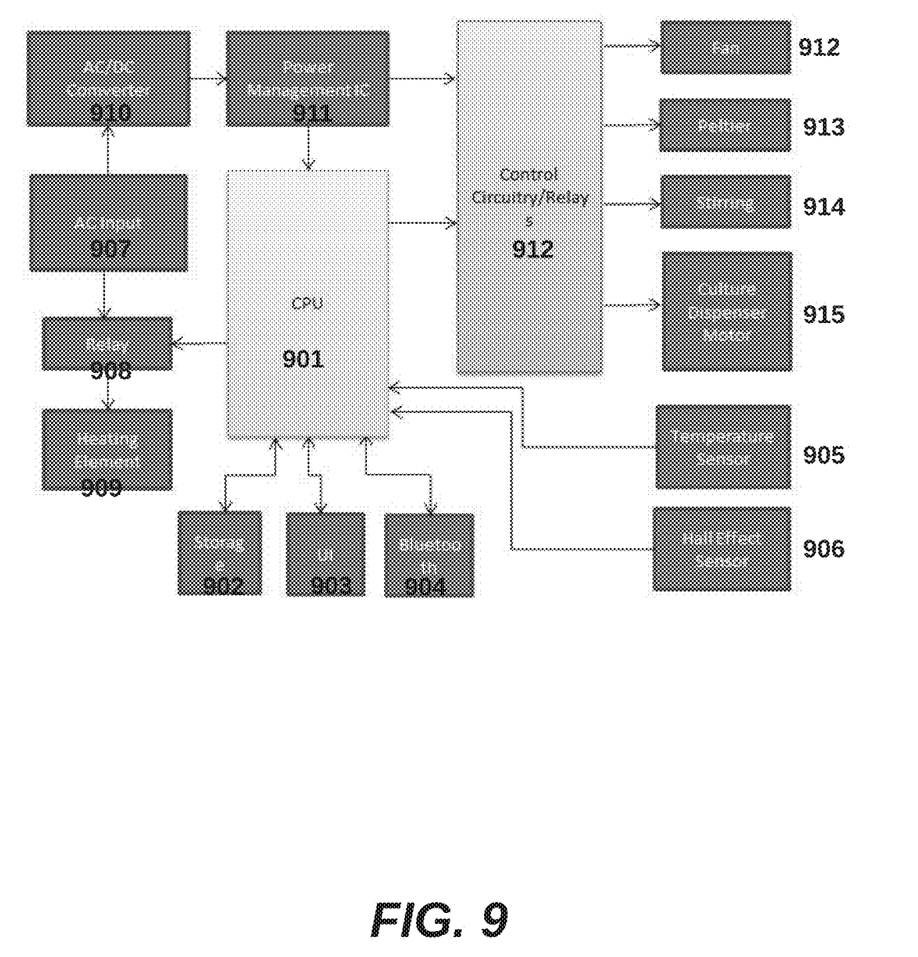
FIG. 9 is a block diagram illustrating the electronic components of yogurt maker devices, according to an embodiment.

FIG. 9 shows an electrical schematic 900 with some major electrical components that are common to the yogurt maker devices, without limitation. A CPU 901, can comprise a standard PC processor, a mobile processor, or a specialized processor or ASIC. The CPU 901 receives inputs from storage 902, user interface 903, Bluetooth module 904 (alternatively can be an Ethernet, USB, Wi-Fi module or the like), temperature sensor 905 and Hall effect sensor 906 for digital controls. An AC input 907 is electrically coupled to a relay 908 which controls a heating element 909, and is also electrically coupled to an AC/DC converter 910 and then to a power management integrated circuit (PMIC) 911. A control circuit/relays 912 receives input from the CPU and the PMIC 911, and outputs to control a fan 912, a Peltier chip 913, a stirring device 914 and a culture dispenser motor 915.

A lid opening controller can be included. A finite state machine optionally tracks different phases of cooking. Additional computing components can include memory devices, input/output interfaces, buses, and non-transitory source code.

The device can receive power using a 110V/220V AC input, for example, which is connected to a wall socket outlet. An AC/DC converter steps down the electrical input to 3 or 4 DC power levels. The PMIC 911 manages power requirements for the host system to ensure maximum current rating of power supply unit is not exceeded.

II. External Connectivity for the Yogurt Maker Devices (FIG. 10)

Figure 10:
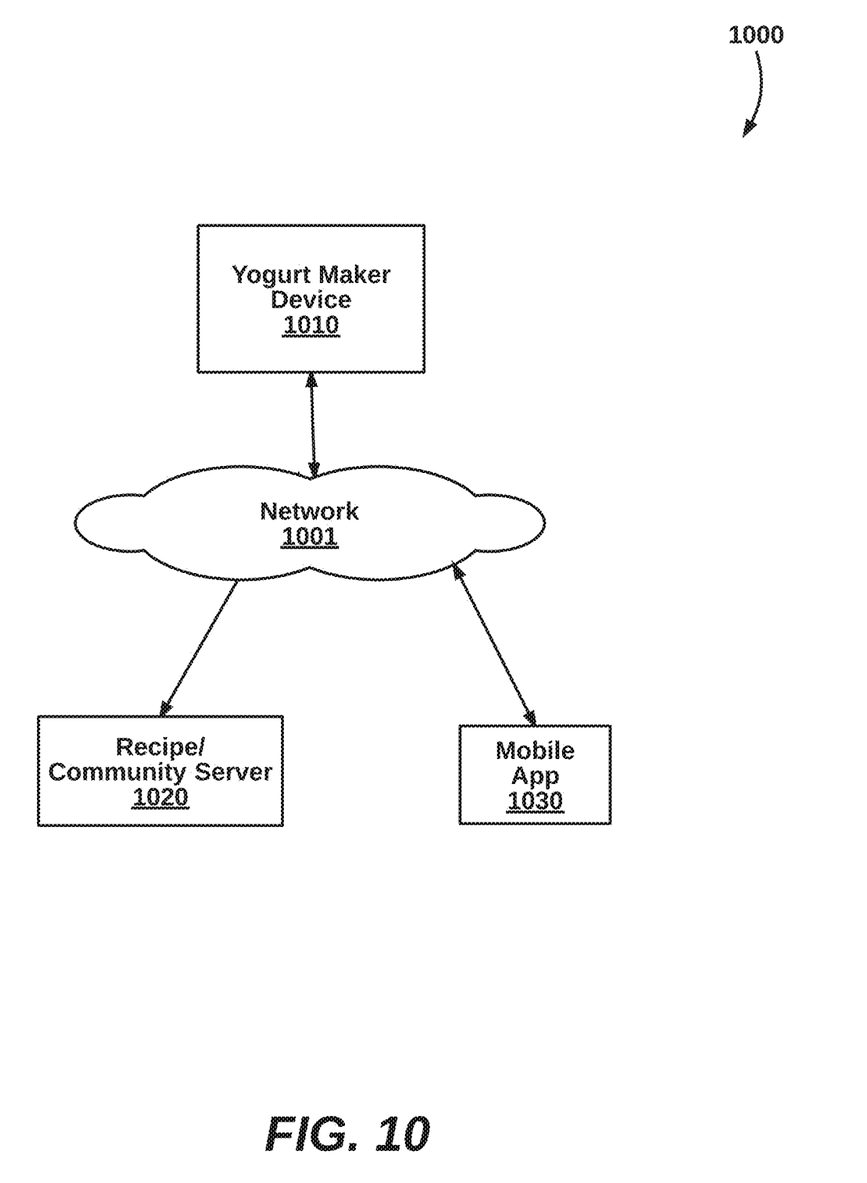
FIG. 10 is a block diagram illustrating network connectivity of a yogurt maker appliance, according to an embodiment.

FIG. 10 illustrates external connectivity functions of yogurt maker devices. A network architecture 1000 includes a yogurt maker device 1010, a recipe/community server 1020, and a mobile app 1030. The yogurt maker device 1010 can be coupled to a network 1001 with a wired or wireless connection.

The recipe/community server 1020 hosts a database of recipe files from various sources. A user of the yogurt maker device 1010 can upload recipe files, along with other members of the community, for sharing. Some users allow public domain user of recipe files while others users require a one time or per use fee for recipe files.

The mobile app 1030 can provide remote control for a user of the yogurt maker device 1010. In one embodiment, the mobile app 1030 utilizes the recipe/community server 1020 as a conduit for connecting to the yogurt maker device 1010. The yogurt maker device 1010 can also send messages to the user at the mobile app 1030. For example, a change of phase message, a completion message, or an error alert can be sent through the communication channel.

III. Methods of Operation in the Yogurt Maker Devices (FIG. 11)

Figure 11:
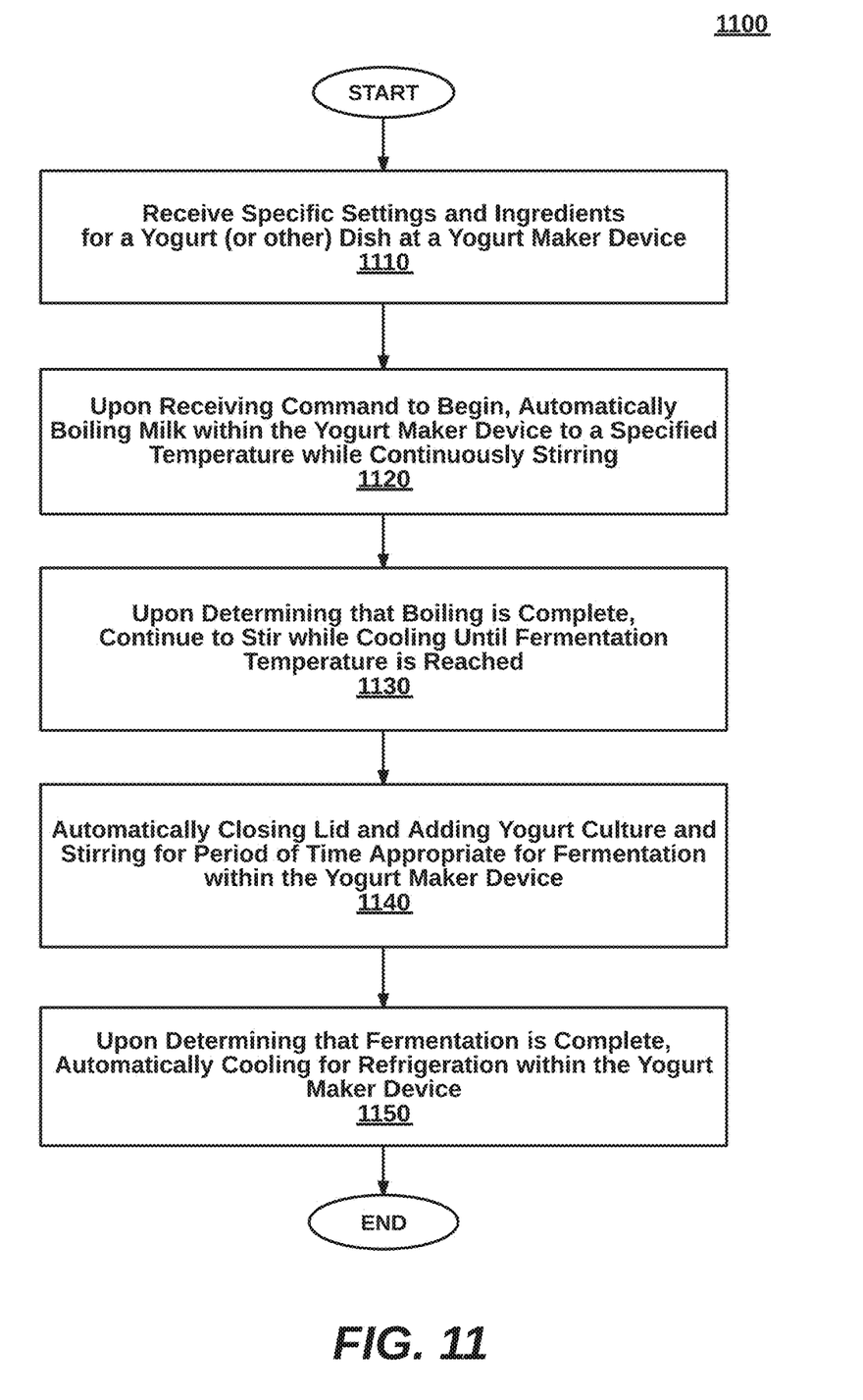
FIG. 11 is a flow chart illustrating a method of automatically preparing yogurt in a yogurt maker appliance, according to an embodiment.

One high-level method of operation in a yogurt maker device is illustrated in FIG. 11. Specific settings for a yogurt dish are received at a yogurt maker device (step 1110). The settings can be entered by a user at a user interface or through a mobile app, or the settings can be automatically programmed from a recipe file. Settings can include boil temperature, fermentation temperature, and durations of phases. Users can attach a top lid assembly. Additionally, user lifts a top lid flap and places the culture holder into the culture dispenser socket 112. Yogurt culture is held separately from the boiling milk.

Upon receiving a command to begin, milk is automatically boiled within the yogurt maker device at a specified temperature while being continuously stirred (step 1120). The command can be entered locally, remotely, or delayed with a timer. In response, a heating element is turned on and stirring begins.

Upon determining that the boiling is complete, the heating element is turned off and stirring is continued while cooling until a fermentation temperature is reached (step 1130). Before the yogurt culture is added, the mixture is cooled from about 180 degrees F. (or as specified by user) to about 111 degrees F. (or user specified) for fermentation (step 1140), in an embodiment. The lid is automatically closed when the yogurt culture is added. In at least one embodiment, upon determining that fermentation is complete, the mixture can be automatically cooled to about 40 degrees F. for refrigeration (step 1140). Users can press stop to turn off the yogurt maker device and take out the yogurt ready for consumption. Upon determination that fermentation is complete, the yogurt maker device automatically cools for refrigeration (step 1150).

As will be understood by those familiar with the art, the invention may be embodied in other specific forms without departing from the spirit or essential characteristics thereof. Likewise, the particular naming and division of the portions, modules, agents, managers, components, functions, procedures, actions, layers, features, attributes, methodologies, data structures and other aspects are not mandatory or significant, and the mechanisms that implement the invention or its features may have different names, divisions and/or formats. The foregoing description, for purpose of explanation, has been described with reference to specific embodiments. However, the illustrative discussions above are not intended to be exhaustive or limiting to the precise forms disclosed. Many modifications and variations are possible in view of the above teachings. The embodiments were chosen and described in order to best explain relevant principles and their practical applications, to thereby enable others skilled in the art to best utilize various embodiments with or without various modifications as may be suited to the particular use contemplated.

We claim:

1. A yogurt making device to autonomously prepare yogurt from ingredients, the yogurt making device comprising:
    an outer shell housing a yogurt vessel that receives milk and houses a yogurt culture container that receives yogurt culture;
    a lid assembly attached to the outer shell to cover the yogurt vessel;
    an input/output device accessible from the outer shell, the input/output device to receive a selection of recipe parameters;
    a processor within or attached to the outer shell;
    a heating element, attached within the outer shell and communicatively coupled to the processor, to boil milk within the yogurt vessel using a temperature sensor as feedback and for maintaining a predefined boiling temperature for a predefined period of boiling time;
    a stirring element, attached within the outer shell and communicatively coupled to the processor, to continuously stir boiling milk within the yogurt vessel while boiling, and also continuously stirring the milk while cooling to a predefined fermentation temperature;
    a culture container base attached within the outer shell and holding the yogurt culture container and having a motor communicatively coupled to the processor, the culture container base initially in an upright position and covered by the lid assembly to protect against hot vapors from boiling milk, while allowing the hot vapors to escape for cooling,
    wherein responsive to cooling down to the predefined fermentation temperature, the culture container base is automatically tipped from the upright position to automatically pour the yogurt culture into the yogurt vessel, and in response to the culture container base tipping, the lid assembly automatically covers the yogurt vessel in a manner that seals a fermentation process; and
    a cooling element, attached within the outer shell and coupled to the processor, to automatically provide cooling to contents of the yogurt vessel once fermentation is complete.

2. The yogurt making device of claim 1, wherein the lid assembly covers the yogurt culture container in a manner that insulates the yogurt culture from boiling milk, prior to the yogurt culture being poured into the yogurt vessel.

3. The yogurt making device of claim 1, further comprising:
    a power management integrated circuit (PMIC) module to manage access to a primary electrical power of the yogurt making device, including management of overlapping requests from the heating element, the stirring element, and the cooling element.

4. The yogurt making device of claim 1, wherein the boiling temperature for boiling milk is received as a recipe parameter of the selected recipe parameters.

5. The yogurt making device of claim 1, wherein the predefined fermentation temperature is received as a recipe parameter of the selected recipe parameters.

6. The yogurt making device of claim 1, wherein a predefined refrigeration temperature for completed yogurt is 40 degrees Fahrenheit, the completed yogurt being derived from the yogurt culture.

7. The yogurt making device of claim 1, wherein the cooling element comprises a Peltier module, an inner heat-sink, an outer heat-sink and an exhaust fan.

8. The yogurt making device of claim 1, which automatically produces yogurt from ingredients.

9. The yogurt making device of claim 1, wherein a top lid flap and a top lid base of the lid assembly, and the yogurt culture container, are all removable for cleaning after exposure to milk fumes.

10. The yogurt making device of claim 1, wherein a motor powers dispersion of the yogurt culture from the culture container base.

11. The yogurt making device of claim 1, wherein the yogurt vessel is composed for boiling milk, for fermenting the yogurt culture and for storage in a refrigerator.

12. The yogurt making device of claim 1, wherein a base of the yogurt vessel is curved and the stirring element is affixed to a flat bottom surface of the yogurt making device.

13. The yogurt making device of claim 1, wherein the recipe parameters include a setting for thick consistency yogurt processed with an extended boiling time.

* * * * *